United States Patent [19]

Cheng

[11] Patent Number: 5,117,010
[45] Date of Patent: May 26, 1992

[54] PROCESS FOR THE PREPARATION OF ADDITION PRODUCTS OF EPOXIDES AND ALCOHOLS

[75] Inventor: Chi-Wen F. Cheng, New York, N.Y.

[73] Assignee: Ciba-Geigy Corporation, Ardsley, N.Y.

[21] Appl. No.: 745,569

[22] Filed: Aug. 15, 1991

[51] Int. Cl.$^5$ .................. C07D 301/27; C07C 41/03; C07C 43/164
[52] U.S. Cl. .................. 549/516; 568/633; 568/637; 568/638; 568/640; 568/643; 568/644; 568/645; 568/648; 568/649
[58] Field of Search ............ 568/640, 633, 637, 638, 568/643, 644, 645, 646, 649, 678; 549/516

[56] References Cited

U.S. PATENT DOCUMENTS

| | | | |
|---|---|---|---|
| 3,033,818 | 5/1962 | Price et al. | 549/516 |
| 3,298,981 | 1/1967 | Fry et al. | 549/516 |
| 3,784,584 | 1/1974 | Renner et al. | 549/516 |
| 4,215,210 | 7/1980 | Okayama et al. | 568/640 |
| 4,256,844 | 3/1981 | Martin et al. | 568/640 |
| 4,284,574 | 8/1981 | Bagg | 549/556 |
| 4,540,828 | 9/1985 | Yang | 568/678 |
| 4,543,430 | 9/1985 | Falgoux et al. | 568/608 |
| 4,568,774 | 2/1986 | Yang | 568/678 |
| 4,810,808 | 3/1989 | Tomita et al. | 549/516 |

FOREIGN PATENT DOCUMENTS

| | | | |
|---|---|---|---|
| 207203 | 2/1984 | German Democratic Rep. | 549/516 |
| 63974 | 5/1981 | Japan | 549/516 |
| 130576 | 7/1985 | Japan | 549/516 |

*Primary Examiner*—J. E. Evans
*Attorney, Agent, or Firm*—JoAnn Villamizar

[57] ABSTRACT

The present invention relates to the preparation of di-secondary alcohols comprising the reaction of an alcohol and a diglycidyl ether of a dihydric phenol in the presence of a catalyst of the formula (IV):

$$MX \qquad (IV)$$

wherein M is a metal from Groups IB to VIIIB or a metal or metalloid from Groups IIA to VA of the Periodic Chart of Elements or an ammonium ion and X is an anion selected from the group consisting of $BF_4^-$, $PF_6^-$, $AsF_6^-$, $SbF_6^-$, $AlF_4^-$, $TiF_6^{2-}$, $SiF_6^{2-}$, and $ZrF_6^{2-}$ to produce the di-secondary alcohol, which can then be subjected to glycidylation to produce a glycidyl ether, or the reaction of an alcohol, glycol or polyol and epichlorohydrin in the presence of the foregoing catalyst, followed by ring closure employing an alkali to produce a mono- or polyglycidyl ether. The monoglycidyl ether can be further reacted with a dihydric phenol to produce a di-secondary alcohol which is then glycidylized to produce a glycidyl ether.

14 Claims, No Drawings

PROCESS FOR THE PREPARATION OF ADDITION PRODUCTS OF EPOXIDES AND ALCOHOLS

BACKGROUND OF THE INVENTION

U.S. Pat. No. 4,284,574 relates to the preparation of diglycidyl ethers of di-secondary alcohols wherein the di-secondary alcohols are prepared by either (A) reaction of a monoglycidyl ether with a dihydric phenol in the presence of a basic catalyst, such as a tertiary amine, a quaternary ammonium base, an alkali metal hydroxide or quaternary ammonium salt or alternatively (B) reaction between an alcohol and a diglycidyl ether of a dihydric phenol in the presence of a basic catalyst, such as a tertiary amine, a quaternary ammonium base, an alkali metal hydroxide, quaternary ammonium salt or a Lewis acid catalyst, such as boron trifluoride complex or stannic chloride. The di-secondary alcohols are then glycidylized to produce the glycidyl ether. The glycidyl ethers produced in accordance with process (A) exhibit viscosities in the range of about 900 to 1500 cps at 25° C. and those in accordance with process (B) exhibit viscosities in the range of greater than 3,000 cps at 25° C. Lower viscosities are desirable in order to decrease or eliminate the amount of reactive diluent needed and it offers advantages in formulations containing large amounts of fillers.

A study of the suitability of liquid state C-13 NMR for investigating the chemical structures and the reaction course of reaction of diglycidyl ether of bisphenol A with 1,4-butanediol in the presence of magnesium perchlorate and N,N-dimethylbenzylamine is disclosed in *Polymer Bulletin*, Vol. 22, p. 221-226 (1989). Use of magnesium perchlorate is disadvantageous due to its explosive nature and lower catalytic reactivity.

U.S. Pat. No. 4,543,430 discloses a process for the preparation of addition products of epoxides and hydroxylated compounds using as a catalyst a salt of trifluoromethane sulfonic acid.

Applicants have found catalysts for the preparation of addition products of an epoxide and an alcohol which provide products with equivalent or lower viscosities which indicates greater selectivity than those produced in accordance with U.S. Pat. No. 4,543,430.

Accordingly, it is an object of the present invention to provide a process for the production of glycidyl ethers of di-secondary alcohols of low viscosity, high purity and low easily hydrolyzable chlorine content.

It is a further object of the present invention to provide a process for the production of mono- and polyglycidyl ethers of primary alcohols, glycols and polyols.

It is a further object of the present invention to provide a process which reduces or eliminates the explosive hazard associated with the use of magnesium perchlorate as a catalyst in the preparation of di-secondary alcohols and aliphatic glycidyl ethers.

Applicants have surprisingly found that glycidyl ethers of di-secondary alcohols of low viscosity, high purity and low easily hydrolyzable chlorine content are obtained with the process of the present invention.

Various other objects and advantages of this invention will become apparent from the following description thereof.

SUMMARY OF THE INVENTION

The present invention relates to the preparation of di-secondary alcohols comprising the reaction of an alcohol and a diglycidyl ether of a dihydric phenol in the presence of a catalyst of the formula (IV):

$$MX \qquad (IV)$$

wherein M is a metal from Groups IB to VIIIB or a metal or metalloid from Groups IIA to VA of the Periodic Chart of Elements or an ammonium ion and X is an anion selected from the group consisting of $BF_4^-$, $PF_6^-$, $AsF_6^-$, $SbF_6^-$, $AlF_4^-$, $TiF_6^{2-}$, $SiF_6^{2-}$ and $ZrF_6^{2-}$ to produce the di-secondary alcohol, which di-secondary alcohol can then be subjected to glycidylation to produce a glycidyl ether; or the reaction of an alcohol and epichlorohydrin in the presence of the foregoing catalyst, followed by ring closure employing an alkali to produce a mono- or polyglycidyl ether which can be further reacted with a dihydric phenol to produce a di-secondary alcohol which is then glycidylized to produce the glycidyl ether.

DETAILED DESCRIPTION OF THE INVENTION

The present invention relates to a process for the preparation of di-secondary alcohols of the formula (I)

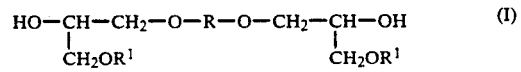

wherein R represents
(i) a phenylene or naphthylene group or
(ii) a radical consisting of two or three phenylene groups linked by one or two carbon-carbon bonds, ether oxygen atoms, sulphur atoms, sulphonyl groups, sulphoxide groups, carbonyl groups, or alkylene groups of 1 to 5 carbon atoms, each phenylene group or each naphthylene group optionally being substituted in the ring or rings by one or two alkyl groups, each of from 1 to 4 carbon atoms, or by one or two chlorine or bromine atoms, and each $R^1$ represents (i) a straight chain or branched alkyl groups of 1 to 16 carbon atoms, which may be substituted by one to four chlorine or bromine atoms, or (ii) a straight chain or branched alkenyl group of 2 to 6 carbon atoms, which may be substituted by one to four chlorine or bromine atoms, or (iii) a phenyl or naphthyl group, optionally substituted in the ring or rings by one or two chlorine or bromine atoms or by from one or two alkyl groups, each of 1 to 4 carbon atoms, and having in all from 6 to 12 carbon atoms, or (iv) a phenylalkyl or naphthylalkyl group, optionally substituted in the ring or rings by one or two chlorine or bromine atoms or by one or two alkyl groups, each of 1 to 4 carbon atoms, said phenylalkyl or naphthylalkyl group having in all from 7 to 12 carbon atoms, or (v) a mononuclear cycloalkyl group of 3 to 6 carbon atoms, or (vi) a mononuclear cycloalkylalkyl group of from 4 to 10 carbon atoms comprising reacting an alcohol of the formula II

R¹OH      (II)

wherein R¹ is defined hereinabove with a diglycidyl ether of a dihydric phenol of the formula III

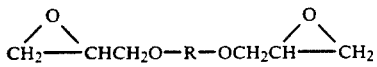
(III)

wherein R is defined hereinabove in the presence of a catalyst of the formula IV

MX      (IV)

wherein M is a metal from Groups IB to VIIB or a metal or metalloid from Groups IIA to VA of the Periodic Chart of Elements or an ammonium ion and X is an anion selected from the group consisting $BF_4^-$, $PF_6^-$, $AsF_6^-$, $SbF_6^-$, $AlF_4^-$, $TiF_6^{2-}$, $SiF_6^{2-}$ and $ZrF_6^{2-}$ producing said di-secondary alcohol.

The present invention further relates to a process for the preparation of diglycidyl ethers of di-secondary alcohols of the formula V

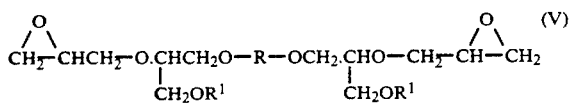
(V)

where R represents (i) a phenylene or naphthylene group or (ii) a radical consisting of two or three phenylene groups linked by one or two carbon-carbon bonds, ether oxygen atoms, sulphur atoms, sulphonyl groups, sulphoxide groups, carbonyl groups, or alkylene groups of 1 to 5 carbon atoms, each phenylene group or each naphthylene group optionally being substituted in the ring or rings by one or two alkyl groups, each of from 1 to 4 carbon atoms, or by one or two chlorine or bromine atoms, and each R¹ represents (i) a straight chain or branched alkyl groups of 1 to 16 carbon atoms, which may be substituted by one to four chlorine or bromine atoms, or (ii) a straight chain or branched alkenyl group of 2 to 6 carbon atoms, which may be substituted by one to four chlorine or bromine atoms, or (iii) a phenyl or naphthyl group, optionally substituted in the ring or rings by one or two chlorine or bromine atoms or by from one or two alkyl groups, each of 1 to 4 carbon atoms, and having in all from 6 to 12 carbon atoms, or (iv) a phenylalkyl or naphthylalkyl group, optionally substituted in the ring or rings by one or two chlorine or bromine atoms or by one or two alkyl groups, each of 1 to 4 carbon atoms, said phenylalkyl or naphthylalkyl group having in all from 7 to 12 carbon atoms, or (v) a mononuclear cycloalkyl group of 3 to 6 carbon atoms, or (vi) a mononuclear cycloalkylalkyl group of from 4 to 10 carbon atoms comprising the steps of (a) reacting an alcohol of the formula II

R¹OH      (II)

wherein R¹ is defined hereinabove with a diglycidyl ether of a dihydric phenol of the formula III

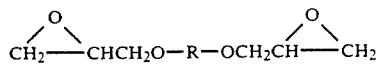
(III)

wherein R is defined hereinabove in the presence of a catalyst of the formula IV

MX      (IV)

wherein M is a metal from Groups IB to VIIB or a metal or metalloid from Groups IIA to VA of the Periodic Chart of Elements or an ammonium ion and X is an anion selected from the group consisting of $BF_4^-$, $PF_6^-$, $AsF_6^-$, $SbF_6^-$, $AlF_4^-$, $TiF_6^{2-}$, $SiF_6^{2-}$ and $ZrF_6^{2-}$ producing a di-secondary alcohol; and (b) reacting said di-secondary alcohol with epichlorohydrin in the presence of an alkali and a phase transfer catalyst to produce said glycidyl ether of a di-secondary alcohol of the formula V.

Preferably, alcohols wherein R¹ is an alkyl group of 1 to 14 carbon atoms, an allyl group, a cyclohexyl group, or a benzyl group are employed. Particularly preferred are alcohols wherein R¹ is an alkyl group of 1 to 14 carbon atoms.

Preferred diglycidyl ethers of a dihydric phenol are those wherein R is a m- or p-phenylene group or a radical consisting of two phenylene rings linked in the o—o', o—p', or p—p' position by an alkylene group of 1 to 4 carbon atoms. Especially preferred diglycidyl ethers of a dihydric phenol are those wherein R represents a group of the formula

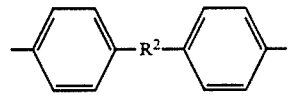

where R² represents a methylene or isopropylidene group, and those where each R¹ represents an alkyl group of from 1 to 12 carbon atoms, more particularly of from 1 to 6 carbon atoms.

At least two moles of alcohol, preferably about 2 to about 6 moles of alcohol and most preferably 4 moles of alcohol are used per mole of diglycidyl ether of a dihydric phenol.

Preferred catalysts of the formula (IV) are those wherein M is a metal selected from the group consisting of copper, zinc, iron, magnesium, silver and calcium or a metalloid such as tin or arsenic or an ammonium ion and X is $BF_4^-$, $SiF_6^{2-}$ or $PF_6^-$. Particularly preferred catalysts are $Sn(BF_4)_2$, $Fe(BF_4)_2$, $Ca(BF_4)_2$, $Zn(BF_4)_2$, $Mg(BF_4)_2$, $Cu(BF_4)_2$, $NH_2BF_4$, $MgSiF_6$ and $AgPF_6$. Most particularly preferred are $Sn(BF_4)_2$, $Fe(BF_4)_2$, $Ca(BF_4)_2$, $Zn(BF_4)_2$, $Mg(BF_4)_2$, $Cu(BF_4)_2$, $NH_4BF_4$ and $AgPf_6$.

· The reaction of the alcohol with the diglycidyl ether of a dihydric phenol is effected by heating the reactants at a temperature in the range of about 50° to 130° C., preferably about 70° to about 120° C., and most preferably about 90° to about 110° C., without solvent.

In the preparation of teh diglycidyl ether of the formula V, the residual alcohol remaining after completion of step (a) is removed by distillation.

The di-secondary alcohol can then be reacted in step (b) with about 2 to about 15 moles, preferably, 6 to about 12 moles, most preferably 10 moles of epichlorohydrin in the presence of about 2 to about 3 moles, preferably about 2 to about 2.2 moles, most preferably about 2.0 to about 2.1 moles of an alkali and in the presence of a phase transfer catalyst at a temperature in the range of about 30° to 90° C., preferably about 40° to about 65° C., and most preferably about 50° to about 55° C. The reaction may be carried out in the presence of a solvent such as a hydrocarbon, an ether, or a ketone, but use of an excess of epichlorohydrin as the solvent is preferred.

Suitable alkali include sodium hydroxide, potassium hydroxide, sodium carbonate, potassium carbonate or a mixture thereof. Sodium hydroxide is preferred.

Suitable phase transfer catalysts include tetraalkylammonium halides such as methyltrioctylammonium chloride, methyltridecylammonium chloride or tetramethylammonium chloride or a tertiary amine or quaternary ammonium base such as benzyltrimethylammonium or a quaternary ammonium salt such as benzyltrimethylammonium chloride. Benzltrimethylammonium chloride is preferred. The phase transfer catalyst is generally used in an amount of about 0.1 to about 5 wt %, preferably about 0.5 to about 2.0 wt % and most preferably about 1.0 to about 1.5 wt % based upon the total weight of the reactants.

The invention further relates to a process for the preparation of a mono- or polydiglycidyl ether comprising (a) reacting a glycol, a polyol of the formula

HOH$_2$C—R$^1$—CH$_2$OH or an alcohol of the formula II

R$^1$OH  (II)

wherein R$^1$ is defined hereinabove with epichlorohydrin in the presence of the foregoing catalyst to produce a mono- or polychlorohydrin ether and (b) reacting said mono- or polychlorohydrin ether with an alkali to produce a mono- or polyglycidyl ether.

The invention still further relates to a process for the preparation of a diglycidyl ether of a di-secondary alcohol of the formula V comprising the steps of (a) reacting an alcohol of the formula II

R$^1$OH  (II)

wherein R$^1$ is defined hereinabove with epichlorohydrin in the presence of the foregoing catalyst to produce a monochlorohydrin ether, (b) reacting said monochlorohydrin ether with an alkali to produce a monoglycidyl ether, (c) reacting said monoglycidyl ether with a dihydric phenol of the formula (VI)

HO—R—OH  (VI)

wherein R is defined hereinabove in the presence of a phase transfer catalyst to produce a di-secondary alcohol; and (d) reacting said di-secondary alcohol with epichlorohydrin in the presence of an alkali and a phase transfer catalyst to produce said glycidyl ether of a di-secondary alcohol of the formula V.

Preferably, alcohols wherein R$^1$ is an alkyl group of 1 to 14 carbon atoms, an allyl group, a cyclohexyl group, or a benzyl group are employed. Particularly preferred are alcohols wherein R$^1$ is an alkyl group of 1 to 14 carbon atoms.

At least one mole of alcohol, preferably about 1 to about 2 moles of alcohol, most preferably about 1.0 to about 1.15 moles of alcohol are used per mole of epichlorohydrin in step (a).

Preferred catalysts of the formula (IV) are those wherein M is a metal selected from the group consisting of copper, zinc, iron, magnesium, silver and calcium or a metalloid such as tin or arsenic or an ammonium ion and X is BF$_4^-$, SiF$_6^{2-}$ or PF$_6^-$. Particularly preferred catalysts are Sn(BF$_4$)$_2$, Fe(BF$_4$)$_2$, Ca(BF$_4$)$_2$, Zn(BF$_4$)$_2$Mg(BF$_4$)$_2$, Cu(BF$_4$)$_2$, NH$_2$BF$_4$, MgSiF$_6$ and AgPF$_6$. Most particularly preferred are Sn(BF$_4$)$_2$, Fe(BF$_4$)$_2$, Ca(BF$_4$)$_2$, Zn(BF$_4$)$_2$, Mg(BF$_4$)$_2$, Cu(BF$_4$)$_2$, NH$_4$BF$_4$ and AgPF$_6$.

The reaction of the alcohol with the epichlorohydrin in step (a) is effected by heating the reactants at a temperature in the range of about 50° to 120° C., preferably about 90° to about 115° C., and most preferably about 110° to about 115° C., without solvent.

The reaction of the monochlorhydrin ether with an alkali in step (b) is effected by heating the reactants at a temperature in the range of about 30° to 90° C., preferably about 50 to about 70° C., and most preferably about 60° to about 65° C.

Suitable alkali include sodium hydroxide, potassium hydroxide, sodium carbonate, potassium carbonate or a mixture thereof. Sodium hydroxide is preferred. About 1.0 to about 1.5 moles of alkali, preferably about 1.0 to about 1.2 moles of alkali, and most preferably about 1.0 to about 1.01 moles of alkali are used.

In the preparation of the diglycidyl ether of the formula V, the monoglycidyl ether is then reacted in step (c) with about 0.10 to about 0.50 moles, preferably, 0.3 to about 0.5 moles, most preferably about 0.45 to about 0.50 moles of a dihydric phenol in the presence of a phase transfer catalyst at a temperature in the range of about 30° to 90° C., preferably about 40° to about 65° C., and most preferably about 50° about 55° C.

Preferred dihydric phenols are those wherein R is a m- or p-phenylene group or a radical consisting of two phenylene rings linked in the o—o', o—p', or p—p' position by an alkylene group of 1 to 4 carbon atoms. Especially preferred diglycidyl ethers of a dihydric phenol are those wherein R represents a group of the formula

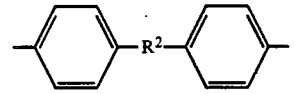

where R$^2$ represents a methylene or isopropylidene group, and those where each R$^1$ represents an alkyl group of from 1 to 12 carbon atoms, more particularly of from 1 to 6 carbon atoms.

Suitable phase transfer catalysts include tetra-akylammonium halides such as methyltrioctylammonium chloride, methyltridecylammonium chloride or tetramethylammonium chloride or a tertiary amine or quaternary ammonium base such as benzyltrimethylammonium or a quaternary ammonium salt such as benzyltrimethylammonium chloride. Benzyltrimethylammonium. chloride is preferred. The phase transfer catalyst is generally used in an amount of about 0.1 to about 5 wt %, preferably about 0.5 to about 2.0 wt % and most preferably about 1.0 to about 1.5 wt % based upon the total weight of the reactants.

The di-secondary alcohol is then reacted in step (d) with about 2 to about 15 moles, preferably, 6 to about 12 moles, most preferably 10 moles of epichlorohydrin in the presence of about 2 to about 3 moles, preferably about 2 to about 2.2 moles, most preferably about 2 to about 2.1 moles of an alkali and in the presence of a phase transfer catalyst at a temperature in the range of about 30° to 90° C., preferably about 40° to about 65° C., and most preferably about 50° about 55° C. The reaction may be carried out in the presence of a solvent such as a hydrocarbon, an ether, or a ketone, but use of an excess of epichlorohydrin as the solvent is preferred.

Suitable alkali include sodium hydroxide, potassium hydroxide, sodium carbonate, potassium carbonate or a mixture thereof. Sodium hydroxide is preferred.

Suitable phase transfer catalyst include tetra-alkylammonium halides such as methyltrioctylammonium chloride, methyltridecylammonium chloride or tetramethylammonium chloride or a tertiary amine or quaternary ammonium base such as benzyltrimethylammonium or a quaternary ammonium salt such as benzyltrimethylammonium chloride. Benzyltrimethylammonium chloride is preferred. The phase transfer catalyst is generally used in an amount of about 0.1 to about 5 wt %, preferably about 0.5 to about 2.0 wt % and most preferably about 1.0 to about 1.5 wt % based upon the total weight of the reactants.

Particularly preferred diglycidyl ethers of di-secondary alcohols which are prepared by the processes of the present invention include the following specific examples:

2,2-bis(p-(3-butoxy-2-glycidyloxypropyloxy)phenyl)-propane;
2,2-bis(p-(3-methoxy-2-glycidyloxypropyloxy)phenyl)-propane;
2,2-bis(p-(3-ethoxy-2-glycidyloxypropyloxy)phenyl)-propane;
2,2-bis(p-(3-dodecyloxy-2-glycidyloxypropyloxy)-phenyl)-propane;
2,2-bis(p-(3-tetradecyloxy-2-glycidyloxypropyloxy)-phenyl)-propane;
2,2-bis(p-(3-benzyloxy-2-glycidyloxypropyloxy)-phenyl)propane;
bis(p-(3-butoxy-2-glycidyloxypropyloxy)phenyl)methane;
1,3-bis(3-phenoxy-2-glycidyloxypropyloxy)benzene;
bis(p-(3-butoxy-2-glycidyloxypropyloxy)phenyl)sulphone;
2,2-bis(p-(3-cyclohexyloxy-2-glycidyloxypropyloxy)phenyl)propane;
2,2-bis(4-(3-butoxy-2-glycidyloxypropyloxy)-3,5-dibromophenyl)propane;
2,2-bis(p-(3-allyloxy-2-glycidyloxypropyloxy)phenyl)-propane;
2,2-bis(p-(3-benzyloxy-2-glycidyloxypropyloxy)-phenyl)propane;
1,3-bis(2-glycidyloxy-3-phenoxypropyloxy)benzene; and
2,2-bis(p-(3-phenoxy-2-glycidyloxypropyloxy)phenyl)-propane.

The glycidyl ethers of the formula V and the polyglycidyl ethers are curable resins and are particularly suitable for use in castings. Suitable methods and compositions in which the glycidyl ethers of formula V find utility are known in the art as set forth in U.S. Pat. No. 4,284,574, which is hereby incorporated by reference.

EXAMPLE 1

(a) Preparation of Di-Secondary Alcohol 323 ml of 1-butanol and 0.41 gm of $Sn(BF_4)_2$(50% in water) is charged to a 1 liter 3-neck round bottom flask equipped with a mechanical stirrer, thermometer, thermoregulator, condenser, dropping funnel and nitrogen inlet. 200 gm of DER 332 (diglycidyl ether of Bisphenol A from Dow Chemical Company, Midland, Mich.) is slowly added over a period of about 3–4 hours while maintaining the temperature at 105° C. with stirring. The reaction is continued until the epoxy value drops to $\leq 0.002$ eq/100 g, which usually takes about 3 to 4 hours with stirring. The excess 1-butanol is then distilled to dryness with high vacuum while maintaining the pot temperature below 110° C. 210 ml of 1-butanol is recovered (theoretical = 215 ml).

(b) Preparation of Diglycidyl Ether

The reaction product of (a), 1 liter of epichlorohydrin and 20 gm of benzyltrimethylammonium chloride (BTMAC) dissolved in 12 ml of water are charged to a 2 liter 3-neck round bottom flask equipped with a mechanical stirrer, thermometer, thermoregulator, condenser, Dean-Stark Trap and dropping funnel. The mixture is then heated to about 50° to 55° C. at high vacuum of 70 torr with stirring resulting in a vigorous reflux of the epichlorohydrin. 109 gm of NaOH (50% solution) is slowly added to the mixture over a period of 2 hours. The water/epichlorohydrin mixture is removed by distillation as soon as the azeotrope is formed. Upon completion of the addition, the epichlorohydrin is returned to the reaction mixture and the reaction is allowed to continue for an additional 1.5 hours. The reaction mixture is then cooled to room temperature and washed with 300 ml of ice water and separated. The organic layer is then washed with another 300 ml of water and the pH adjusted to about 5–6 using 10% aqueous acetic acid. The organic layer is then washed a third time with 300 ml of water and separated. The epichlorohydrin is then removed by distillation at reduced pressure (from 70 to 2 torr). The final distillation condition about less than 5 torr/110° C. The distillation is continued until no volatile could be distilled to ensure the complete removal of the epichlorohydrin. The yield is 330 gm. The epoxy value is 0.306 eq/100 g and the viscosity is 1310 cps at 25° C.

EXAMPLES 2–15

Different catalysts in the amounts specified in Table 1 are used in the procedure of Example 1 providing products with the properties set forth in Table 1. Examples 14 and 15 are provided as comparative experiments.

TABLE 1

| Example | Catalyst | $\alpha$ Conc | $\beta$ Time | Product Property E.V. (eq/100 g) | $\gamma$ Viscosity |
|---|---|---|---|---|---|
| 2 | $Fe(BF_4)_2$ | 0.2% | 3 hr | 0.291 | 1300 |
| 3 | $Zn(BF_4)_2$ | 0.1% | 7 hr | 0.301 | 1879 |
| 4 | $Zn(BF_4)_2$ | 0.1% | 6 hr | 0.300 | 1902 |
| 5 | $Ca(BF_4)_2$ | 0.2% | 2 hr | 0.308 | 1786 |
| 6 | $Ca(BF_4)_2$ | 0.4% | 0 hr | 0.291 | 1905 |
| 5 | $Mg(BF_4)_2$ | 0.2% | 2 hr | 0.311 | 2083 |
| 6 | $NH_4BF_4$ | 1.0% | 11 hr | 0.308 | 2102 |
| 7 | $Sn(BF_4)_2$ | 0.1% | 3 hr | 0.308 | 1265 |
| 8 | $Sn(BF_4)_2$ | 1.0% | 0 hr | 0.277 | 2439 |
| 9 | $Cu(BF_4)_2$ | 0.1% | 4 hr | 0.301 | 1265 |
| 10 | $Mg(PF_6)_2$ | 1.0% | 6 hr | 0.284 | 2773 |
| 11 | $AgPF_6$ | 1.0% | 3 hr | 0.305 | 1501 |

TABLE 1-continued

| Example | Catalyst | α Conc | β Time | Product Property E.V. (eq/100 g) | γ Viscosity |
|---|---|---|---|---|---|
| 12 | NH$_4$PF$_6$ | 2.0% | 11 hr | 0.314 | 3107 |
| 13 | MgSiF$_6$ | δ3.0% | 4 hr | 0.289 | 2620 |
| 14 | Zn(CF$_3$SO$_3$)$_2$ | 0.15% | 4 hr | 0.275 | 3402 |
| 15 | Mg(CF$_3$SO$_3$)$_2$ | 2.0% | 0 hr | 0.271 | 2727 |

α-Based on the weight of the diglycidyl ether of Bisphenol A used/40-50% aqueous solution
β-Time needed for Stage I (after addition of the diglycidyl ether of Bisphenol A)
γ-Viscosity in centipoise measured at 25° C.
δ-1.0% of the catalyst is added initially and after all the diglycidyl ether of Bisphenol A is added, another 1.0% of the catalyst is added. The final 1.0% of the catalyst is added 2 hours later.

EXAMPLE 16

(a) Preparation of Monochlorohydrin Ether 370 ml 1-butanol and 1.8 gm of Sn(BF$_4$)$_2$(50% aqueous solution) are charged to a 1 liter 3-neck round bottom flask equipped with a mechanical stirrer, thermometer, thermoregulator, condenser, dropping funnel and nitrogen inlet. 344 gm of epichlorohydrin is slowly added over a period of about 4 hours while maintaining the temperature at 115° C. with stirring. The reaction is continued until the epoxy value of the reaction mixture is less than 0.002 eq/100 g.

(b) Preparation of Monoglycidyl Ether

The reaction product of (a) is charged to a 2 liter 3-neck round bottom flask equipped with a mechanical stirrer, thermometer, thermoregulator, condenser, Dean-Stark Trap and dropping funnel. The reaction mixture is then heated to about 60° to 65° C. with vigorous stirring. 351.2 gm of a 50% solution of NaOH is slowly added to the mixture as follows: after 80 gm of caustic is added, 30 ml of water is added to help stirring; after another 80 g of caustic is added, another 30 ml of water is added and finally the remainder of the caustic is added. The reaction mixture is then maintained at about 60°-65° C. for 2 hours. The reaction mixture is then cooled to room temperature and washed with 300 ml of water and separated. The organic layer is then washed with 200 ml of 15% NaCl solution and the pH adjusted to about 5-6 using 10% aqueous acetic acid. 35 gm of azeotropic mixture of product (butyl glycidyl ether) with water is then removed by distillation at about 70-80 torr. The distillation head is from 40° to about 70° C. with a pot temperature of 80° C. 435 gm of butyl glycerol ether (with an epoxy value of 0.726 Eq/100 gm and an average hydrolyzable chloride of 329.1 ppm) is distilled off at 70-80 torr at 98 to about 105° C. with a pot temperature of 120 to about 140° C. The 68.5 g of residue is purified on Kugelohr providing a yield of 35 gm of distilled product with an epoxy value of 0.368 Eq/100 gm.

(c) Preparation of Di-Secondary Alcohol 100 g of the reaction product of (b), 292.62 of bisphenol A and 10 gm of benzyltrimethylammonium chloride (BTMAC) are charged to a 3 liter 3-neck round bottom flask equipped with a mechanical stirrer, thermometer, thermoregulator, condenser, Dean-Stark Trap and dropping funnel. The mixture is slowly heated to about 100° C. while monitoring the exotherm which is not permitted to exceed 130° C. The temperature is then maintained at 125° C. and an additional 300 g of the reaction product of (b) slowly added over a period of one hour. After the addition is completed, the mixture is heated to attain a constant temperature of 125° C. The reaction is continued for about 2 hours. The theoretical epoxy value is 0.03455 to about 0.0413 Eq/100 gm and the actual epoxy value is 0.045 Eq/100 gm. The excess butyl glycidyl ether (product from (a)) is distilled to dryness with high vacuum while maintaining the pot temperature below 110° C. 47 gm of butyl glycidyl ether is recovered (theoretical 41 gm).

What is claimed is:

1. A process for the preparation of di-secondary alcohols of the formula (I)

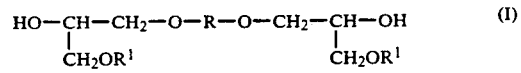

wherein R represents
(i) a phenylene or naphthylene group or
(ii) a radical consisting of two or three phenylene groups linked by one or two carbon-carbon bonds, ether oxygen atoms, sulphur atoms, sulphonyl groups, sulphoxide groups, carbonyl groups, or alkylene groups of 1 to 5 carbon atoms,
each phenylene group or each naphthylene group optionally being substituted in the ring or rings by one or two alkyl groups, each of from 1 to 4 carbon atoms, or by one or two chlorine or bromine atoms, and each R$^1$ represents
(i) a straight chain or branched alkyl group of 1 to 16 carbon atoms, which may be substituted by one to four chlorine or bromine atoms, or
(ii) a straight chain or branched alkenyl group of 2 to 6 carbon atoms, which may be substituted by one to four chlorine or bromine atoms, or
(iii) a phenyl or naphthyl group, optionally substituted in the ring or rings by one or two chlorine or bromine atoms or by from one or two alkyl groups, each of 1 to 4 carbon atoms, and having in all from 6 to 12 carbon atoms, or
(iv) a phenylalkyl or naphthylalkyl group, optionally substituted in the ring or rings by one or two chlorine or bromine atoms or by one or two alkyl groups, each of 1 to 4 carbon atoms, said phenylalkyl or naphthylalkyl group having in all from 7 to 12 carbon atoms, or
(v) a mononuclear cycloalkyl group of 3 to 6 carbon atoms, or
(vi) a mononuclear cycloalkylalkyl group of from 4 to 10 carbon atoms comprising reacting an alcohol of the formula II

wherein R$^1$ is defined hereinabove with a diglycidyl ether of a dihydric phenol of the formula III

wherein R is defined hereinabove in the presence of a catalyst of the formula IV

wherein M is a metal from Groups IB to VIIIB or a metal or metalloid from Groups IIA to VA of the Periodic Chart of Elements or an ammonium ion and X is an anion selected from the group consisting $BF_4^-$, $PF_6^-$, $AsF_6^-$, $SbF_6^-$, $AlF_4^-$, $TiF_6^{2-}$, $SiF_6^{2-}$ and $ZrF_6^{2-}$ producing said di-secondary alcohol.

2. A process according to claim 1 wherein said alcohol is an alcohol wherein $R^1$ is an alkyl group of 1 to 14 carbon atoms, an allyl group, a cyclohexyl group, or a benzyl group.

3. A process according to claim 1 wherein said diglycidyl ether of a dihydric phenol is one wherein R is a m- or p-phenylene group or a radical consisting of two phenylene rings linked in the o—o', o—p', or p—p' position by an alkylene group of 1 to 4 carbon atoms.

4. A process according to claim 1 wherein about 2 to 6 moles of alcohol are used per mole of glycidyl ether of a dihydric phenol.

5. A process according to claim 1 wherein M is selected from the group consisting of copper, zinc, iron, magnesium, silver, calcium, tin, arsenic and ammonium ion and X is $BF_4^-$, $SiF_6^{2-}$ or $PF_6^-$.

6. A process according to claim 1 wherein MX is $Sn(BF_4)_2 Fe(BF_4)_2$, $Ca(BF_4)_2 Zn(BF_4)_2$, $Mg(BF_4)_2$, $NH_4BF_4$ or $AgPF_6$.

7. A process for the preparation of diglycidyl ethers of di-secondary alcohols of the formula V

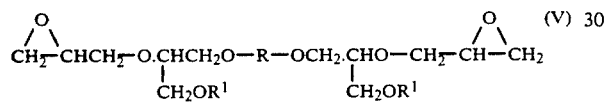

where R represents
(i) a phenylene or naphthylene group or
(ii) a radical consisting of two or three phenylene groups linked by one or two carbon-carbon bonds, ether oxygen atoms, sulphur atoms, sulphonyl groups, sulphoxide groups, carbonyl groups, or alkylene groups of 1 to 5 carbon atoms,
each phenylene group or each naphthylene group optionally being substituted in the ring or rings by one or two alkyl groups, each of from 1 to 4 carbon atoms, or by one or two chlorine or bromine atoms, and each $R^1$ represents
(i) a straight chain or branched alkyl group of 1 to 16 carbon atoms, which may be substituted by one to four chlorine or bromine atoms, or
(ii) a straight chain or branched alkenyl group of 2 to 6 carbon atoms, which may be substituted by one to four chlorine or bromine atoms, or
(iii) a phenyl or naphthyl group, optionally substituted in the ring or rings by one or two chlorine or bromine atoms or by from one or two alkyl groups, each of 1 to 4 carbon atoms, and having in all from 6 to 12 carbon atoms, or
(iv) a phenylalkyl or naphthylalkyl group, optionally substituted in the ring or rings by one or two chlorine or bromine atoms or by one or two alkyl groups, each of 1 to 4 carbon atoms, said phenylalkyl or naphthylalkyl group having in all from 7 to 12 carbon atoms, or
(v) a mononuclear cycloalkyl group of 3 to 6 carbon atoms, or
(vi) a mononuclear cycloalkylalkyl group of from 4 to 10 carbon atoms comprising the steps of
(a) reacting an alcohol of the formula II $$R^1OH \quad (II)$$

wherein $R^1$ is defined hereinabove with a diglycidyl ether of a dihydric phenol of the formula III

wherein R is defined hereinabove in the presence of a catalys of the formula IV $$MX \quad (IV)$$

wherein M is a metal from Groups IB to VIIIB or a metal or metalloid from Groups IIA to VA of the Periodic Chart of Elements or an ammonium ion and X is an anion selected from the group consisting $BF_4^-$, $PF_6^{31}$, $AsF_6^-$, $SbF_6^-$, $AlF_4^-$, $TiF_6^{2-}$, $SiF_6^{2-}$ and $ZrF_6^{2-}$ producing a di-secondary alcohol; and
(b) reacting said di-secondary alcohol with epichlorohydrin in the presence of an alkali and a phase transfer catalyst to produce said glycidyl ether of a di-secondary alcohol of the formula V.

8. A process according to claim 7 wherein said alcohol is an alcohol wherein $R^1$ is an alkyl group of 1 to 14 carbon atoms, an allyl group, a cyclohexyl group, or a benzyl group.

9. A process according to claim 7 wherein said diglycidyl ether of a dihydric phenol is one wherein R is a m- or p-phenylene group or a radical consisting of two phenylene rings linked in the o—o', o—p', or p—p' position by an alkylene group of 1 to 4carbon atoms.

10. A process according to claim 7 wherein about 2 to 6 moles of alcohol are used per mole of glycidyl ether of a dihydric phenol.

11. A process according to claim 7 wherein M is selected from the group consisting of copper, zinc, iron, magnesium, silver, calcium, tin, arsenic and ammonium ion and X is $BF_4^-$, $SiF_6^{2-}$ or $PF_6^-$.

12. A process according to claim 7 wherein MX is $Sn(BF_4)_2$ $Fe(BF_4)_2$, $Ca(BF_4)_2$ $Zn(BF_4)_2$, $Mg(BF_4)_2$, $Cu(BF_4)_2$, $NH_4BF_4$ or $AgPF_6$.

13. A process according to claim 7 wherein said di-secondary alcohol is reacted with about 2 to about 15 moles of epichlorohydrin in the presence of about 2 to about 3 moles of sodium hydroxide and in the presence of about 0.1 to about 5 wt % of a phase transfer catalyst selected from the group consisting of a quaternary ammonium base and a quaternary ammonium salt at a temperature in the range of about 30° to 90° C.

14. A process according to claim 7 wherein said phase transfer catalyst is benzyltrimethylammonium chloride.

* * * * *